United States Patent
Senn

(10) Patent No.: US 10,076,390 B2
(45) Date of Patent: Sep. 18, 2018

(54) LIGHT MIXTURE

(71) Applicant: Ivoclar Vivadent AG, Schaan (LI)

(72) Inventor: Bruno Senn, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 291 days.

(21) Appl. No.: 14/349,415

(22) PCT Filed: Oct. 8, 2012

(86) PCT No.: PCT/EP2012/069830
§ 371 (c)(1),
(2) Date: Aug. 6, 2014

(87) PCT Pub. No.: WO2013/050587
PCT Pub. Date: Apr. 11, 2013

(65) Prior Publication Data
US 2014/0356804 A1 Dec. 4, 2014

(30) Foreign Application Priority Data

Oct. 6, 2011 (EP) ..................................... 11184195
Oct. 2, 2012 (EP) ..................................... 12187017

(51) Int. Cl.
| | |
|---|---|
| *A61C 19/00* | (2006.01) |
| *A61C 13/15* | (2006.01) |
| *G02B 6/42* | (2006.01) |
| *G02B 6/02* | (2006.01) |
| *G02B 6/04* | (2006.01) |

(52) U.S. Cl.
CPC ........ *A61C 19/004* (2013.01); *G02B 6/02042* (2013.01); *G02B 6/04* (2013.01); *G02B 6/421* (2013.01); *G02B 6/4298* (2013.01)

(58) Field of Classification Search
CPC .............................. A61C 19/003; A61C 19/004
See application file for complete search history.

(56) References Cited

U.S. PATENT DOCUMENTS

| | | | | |
|---|---|---|---|---|
| 6,046,460 A | * | 4/2000 | Mertins | ................ A61C 19/004 250/504 H |
| 6,658,896 B2 | * | 12/2003 | Galarza | ................ A61C 19/004 65/408 |
| 6,692,250 B1 | | 2/2004 | Decaudin et al. | |

(Continued)

FOREIGN PATENT DOCUMENTS

| | | |
|---|---|---|
| DE | 9017070 U1 | 4/1992 |
| EP | 1031326 A1 | 8/2000 |

(Continued)

*Primary Examiner* — Ralph Lewis
(74) *Attorney, Agent, or Firm* — Ann M. Knab; Thad McMurray

(57) ABSTRACT

The invention relates to a light mixing device for a medical or dental-medical lighting device, in particular for a light curing device for the polymerization of dental masses, which device comprises a housing with a light generation device, as well as a light conductor. The light mixing device (2) comprises a bar-shaped light mixing member (8) with preferably at least one transparent material, in particular glass, as well as a holder (7) by means of which the light mixing device (2) is mountable between the light generation device (1) and the light conductor (3) and is held in position by the light conductor (3) as to be separable therefrom.

33 Claims, 2 Drawing Sheets

(56) References Cited

U.S. PATENT DOCUMENTS

Figure 1:
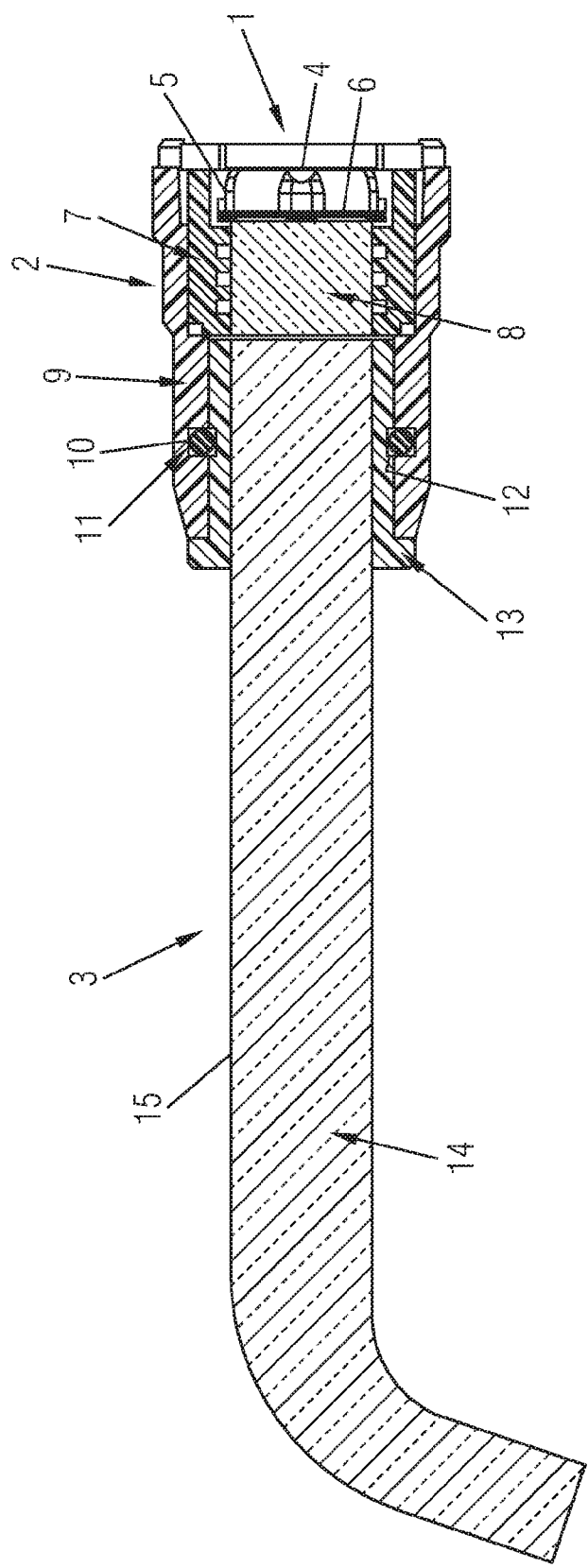

| | | | |
|---|---|---|---|
| 7,182,597 B2 | 2/2007 | Gill et al. | |
| 8,337,200 B2* | 12/2012 | Wang | A61C 19/004 250/492.1 |
| 2004/0141336 A1* | 7/2004 | West | A61C 19/004 362/555 |
| 2006/0045419 A1 | 3/2006 | Matsumura et al. | |
| 2006/0285328 A1 | 12/2006 | Syribeys | |
| 2014/0242538 A1* | 8/2014 | Senn | G02B 6/421 433/29 |

FOREIGN PATENT DOCUMENTS

| | | |
|---|---|---|
| JP | 2003235870 A | 8/2003 |
| JP | 2004001881 A | 1/2004 |
| JP | 2004275276 A | 10/2004 |
| WO | 99/35995 A1 | 7/1999 |
| WO | 02/11640 A2 | 2/2002 |
| WO | 2005/114283 A1 | 12/2005 |
| WO | 2007/057974 A1 | 5/2007 |

* cited by examiner

LIGHT MIXTURE

CROSS-REFERENCE TO RELATED APPLICATIONS

This application is a National Stage application of International patent application PCT/EP2012/069830 filed on Oct. 8, 2012, which claims priority to European patent application No. 11184195.3 filed on Oct. 6, 2011, and to European patent application No. 12187017.4 filed Oct. 2, 2012, the disclosures of which are incorporated herein by reference in their entirety.

The invention relates to the improvement of lighting devices, in particular in the field of medicine and dentistry, as well as the improvement of light curing devices, preferably for the dental-medical use, that are particularly provided with metal semiconductor radiation sources such as light-emitting diodes and that emit radiation in the visual range, UV range and/or the near infrared spectral range.

More specifically, the invention relates to a light mixing device that is particularly suitable for the use in medical or dental-medical lighting devices or light curing devices for the polymerisation of dental masses. The term light, as it is used here in the specification and the claims, not only refers to the electromagnetic radiation in the visible spectral range, but also refers to the electromagnetic radiation in the UV and near infrared range. If in the following the preferably used light-emitting diodes (or LEDs or LED chips) are spoken of, those terms are also intended to include other lighting means and radiation sources that emit visible light, UV-light and/or near infrared light, in particular semiconductor radiation sources that—for reasons of a better readability—are not to be listed at all places.

Such light curing devices have been known for a long time.

One example for the implementation of a light conductor from the 1970ies can be taken from DE 23 52 670. Already at that time, flexible light conductors consisting of a single fiber have been considered to be well known. The document also verifies as known the implementation of light-conducting liquids and of a flexible plastic hose for the provision of a light conductor.

Light conductors that consist of a single fiber and that may also be referred to as a light conductor rod, are basically comparatively stiff or rigid and are thus hard to bend. Light conductors filled with a liquid, on the other hand, are unfavorable or disadvantageous especially in applications in the oral environment as there is the danger that the patient—inadvertently—bites on the light conductor and in this manner causes a leak.

In the 1980ies, but also up to now, one typically has moved on to multiple fiber light conductors; one example mentioned is DE 297 09 785.

Multiple fiber light conductors that are also referred to as multicore light conductors, have the advantage of offering a substantially improved bending property. The dentist is thus able to impart the desired shape to the light conductor on the end side therof in order to obtain the light emission or exit at the desired, partially deep-seated position.

The same applies by the way to the use of light conductors for light sensors for dental cameras, but also for example to the use of light conductors in endoscopes that require narrow radiuses of curvature as well.

It has already been known for a long time that with the aid of optically additive mixtures of base colors such as red, yellow and blue, it is possible to generate white light. This fact is exploited by arranging LEDs of corresponding coloring closely adjacent to one another and by supplying or guiding the light emission thereof to the light conductor.

In fact, so-called white LEDs have become known recently. These, however, are still comparatively expensive at present, and due to the light mixture the exact shade of color can be better adapted to the requirements. It is also possible to select a certain emission spectrum.

If a single LED or a single LED chip are used as the light source, the light emission primarily takes place on the upper side of the LED chip that typically has a size of approximately 1 mm². If a multicore light conductor that typically has a diameter of 6 to 13 mm, is installed in front of the LED chip, the main light emission typically only strikes or impinges on the 6 or 7 inner fibers, whereas only a very small portion of the outer optical fibers are utilized.

In order to prevent such a situation, it has become known to use a collecting lens at the light entry side end of the optical fiber. On the other hand, the additional provision of a collecting lens means two further optical boundary surfaces or interfaces with the respective reflections so that the degree of efficiency decreases.

In both applications mentioned, one therefore gladly resorts to monocore light conductors or light conductor rods, especially since the entire cross-sectional area of the light conductor can be taken by the optical effective medium in case of the monocore technology, in contrast to the yield losses arising from the use of multicore light conductors.

Moreover, document EP 0 549 332 reveals an optical coupling device that permits to homogenize different light intensities between the single fibers of the fibre bundle within one light conducting length consisting of one fiber bundle. For this purpose, the optical coupling device that comprises a light-conducting rod that is bent 180 degrees, is incorporated into the fiber bundle within the light conductor length, the entry end as well as the exit end of the optical coupling device being fixedly connected to the ends of the fiber bundle of the light conducting length via a connection sleeve.

U.S. Pat. No. 6,692,250 describes a light concentrator that taps the light of a plurality of light-emitting diodes via individual thin light conductor fibers, respectively, and reunites them in one fiber bundle, in order to then supply the lighting currents of the individual light-emitting diodes into a bent light conductor rod and to combine them, where a homogenization of the lighting currents of the individual light-emitting diodes and an uniform redistribution takes place between the individual fibers of the fiber bundle.

Contrary hereto, the the object of the invention is to provide a device, in particular for a medical or dental-medical lighting device, in particular for a light curing device for the polymerisation of dental masses, that permits to homogenize and mix the light produced within a light generation device and to distribute the light across the entire cross-sectional area of the light conductor so that a surface at the exit of the light conductor can be evenly or homogeneously illuminated with respect to brightness and spectral distribution. Moreover, this device should also enable an efficient, simple and low-loss feed of the emitted light, such as it is particularly produced by several light emitting diodes or other semiconductor radiation sources, into a light conductor that preferably is embodied as a fiber bundle consisting of many thin individual optical fibers.

A further object of the invention is to provide a suitable arrangement for medical and dental-medical lighting devices, in particular for light curing devices for the polymerisation of dental masses that permits a sterilization of all parts that potentially come into contact with the patient, according to conventional methods of medical technology, and that can also be autoclaved according to particularly all conventional methods without damaging the optical structure, light generation device, electronics or any other components or without losing in quality. In this respect, in particular the aspects of handling of the device during its operation or during the treatment of a patient, respectively, for example by a doctor, specialized medical staff or a dental technician, as well as between the operations or between the treatments of patients, respectively, are to be taken into account, whereas practical routine procedures in connection with the work in dentistry such as sterilization, autoclavation and modification procedures, for example when replacing light conductors, are particularly to be taken into account.

This object is inventively solved for a medical or dental-medical dental lighting device, in particular for a light curing device for the polymerisation of dental masses, with the aid of a light mixing device according to claim 1. Furthermore in claim 13 a corresponding medical or dental-medical lighting device, in particular a light curing device for the polymerisation of dental masses with a corresponding light mixing device according to claim 1, is specified for providing an inventive solution to the object of the invention.

Advantageous further developments emerge from the text of the specification and particularly from the stated subclaims. All disclosed technical features from the description text and subclaims can be freely combined according to the technical knowledge of the skilled person and can be jointly technically implemented in conjunction with the features of the independent claim 1 or 13, respectively.

In this connection, it is particularly favorable that due to the use of the inventive light mixing device, the advantages of monocore and multicore light conductors can be surprisingly achieved simultaneously without incurring the disadvantages to be expected. The poor light mixing present in the case of multicore light conductors is completely avoided, as well as the only partial light impingement on fibers within the fiber bundle that in case of respective devices according to the state of the art has to primarily take place on the central optical fibers in order to keep the bypass losses within a limit. Also, it is not necessary to use a collecting lens on the entry side; rather it is possible to directly feed the light radiation emitted by the one or more LED chips to the light mixing device. Due to the comparatively large light entry surface, the light mixing device completely absorbs the light radiation and guides or feeds it forward.

In this connection it is also possible in a modified embodiment of the invention to connect more than one multicore and/or monocore section of a light conductor with one another. This is favorabe for example, if the light conductor is very long and comprises positions along its extension or run at which it must be heavily bent. At said positions, multicore sections are formed and monocore sections at the rest. Also, it would be conceivable to arrange more of the inventive light mixing devices within the radiation path.

Whereas optical fibers typically offer a light output of 15% less compared to monocore light conductors, it is inventively provided to considerably reduce these output losses. If only the front, thus light exit sided first third of the light conductor is formed to be multicore and the rearward two thirds of the light conductor are formed to be monocore, the yield or output losses are reduced from 15 to 5%.

Also, it is particularly favorable that according to the invention it is prevented that an image of the LED-chips is displayed or imaged by the optical fibers or the multicore light conductor. In the inventive light mixing device, a strong mixing of the supplied light radiation is produced and in this way provides for the homogenization and light standardization.

Thus, a plurality of desired different emission spectra can be provided with the implementation of several LED chips of different color that are arranged in the light generation device of the lighting device or light curing device, and in fact without the need of using an additional collecting lens and further sophisticated or complex homogenization devices. This also particularly applies to the light conductor chips of different color typically arranged in a triangle that for example have their emission maxima in the red, green and blue spectral range and from which any light color may be produced through additive light mixing.

With the aid of the inventive means or device, moreover, all previous problems of the prior art with regard to sterilization by autoclavation, can be avoided, which problems are particularly caused by the high sterilization temperature, temperature changes, high pressures and strong pressure changes as well as the moisturization and re-drying problems of surfaces and cavities, as well as problems with respect to aging and embrittlement of components, inadequate disinfection in gaps and cavities, problems with air-filled or liquid-filled cavities etc.

Moreover, a re-infection of sterilized components may be excluded in a simple manner, as the removable or detachable light conductor can remain in sterile storage containers in a re-infection safe environment till its use. A further advantage is the low space requirement during the autoclavation process as only the light conductors detached from the device must be subjected to the sterilization treatment, whereas also a plurality of contaminated light conductors can be collected expediently, before they are jointly subjected to a treatment in an autoclave.

A further advantage of the inventive solution is that a damage or maladjustment of the optical components in the radiation path of the light guidance of such devices, such as it can occur in the prior art due to heat development during the operation, as well as due to autoclavation, can be reliably avoided. In this connection, so far in the popular lighting and light curing device due to the thermal expansion of the different materials on the one hand—different optical glasses with low expansion coefficients, metal holders and plastic components with high thermal expansion coefficients—strong tensions, cracks, ruptures and maladjustments occured.

A further advantage of the solution according to the invention is that an otherwise mandatory protective glass that reliably protects the light emitting diodes or semiconductor radiation sources, as well as the associated reflectors, from pollution, moisture and damages, can be omitted if instead an inventive light mixing device is arranged. Preferably it is even possible to maintain the tried-and-tested plug-in coupling solution of conventional light conductors according to the prior art having a bushing in the lighting device or light curing device, as well as a sleeve at the light conductor and to further use the tried-and-tested constructional design of the respective devices. Due to the inventive solution there is no enlargement of the structural shape of the devices or a considerable increase in weight so that compactness and handiness of the respective devices can be fully maintained.

Likewise, the inventive solution may be incorporated in all conventional devices at a very low cost and with only minimal constructional changes. Moreover, a very simple assembly or replacement of light conductors in the medical or dental-medical surgery or for example in the dental laboratory is possible. Further, the solution according to the invention is extremely easy to maintain in the service workshop.

Surprisingly, with the inventive light mixing device, despite its simple structure and its very short overall length, i.e. also very short light mixing length within the light mixing member—in particular in interaction with the reflector arrangement in the light generation device of the devices conventionally used in the prior art—as well as due to the multiple phase transition or interfacial interactions of boundary surfaces between solids and again solids in the course of light path of such a device, for example light emitting diode/air, air/reflector, reflector/air, air/protective glass, protective glass/air, air/light mixing member, light mixing member/air, air/fiber bundle—also due to interfacial reflections and resulting running time differences of different radiation bundles in the optical or radiation path and the superimposition thereof, an unexpected high degree of homogenization with respect to the intensity distribution and the spectral emission curves across the entire exit surface of the light conductor fiber bundle may be achieved. At the same time, only very low light losses occur with respect to the entire radiation energy produced by the light emitting diodes till the exit end of the light conductor fiber bundle. Thus, bonding with an optically transparent adhesive between the light mixing member and the fiber bundle may be omitted without any problems without incurring higher light losses.

In this manner, not only the production and operating expenses can be reduced but also in particular handling of the light conducting fiber bundle independent of the light mixing device is facilitated. Due to this, a complete advantageous solution to the object of the invention is possible and the advantages with respect to handling, hygiene and sterilization can be realized.

A solution to the sterilization problems that has been proposed earlier, namely to use autoclavable coatings or disposable coatings over the light conducting devices with its known disadvantages becomes obsolete due to the proposed solution. All problems with respect to the different coefficients of expansion of the materials glass, plastics, metal that in particular occur at the junctions between the different components in the optical radiation path, that is for example between the light mixing member and the fiber bundle, can be reliably avoided using the solution according to the invention.

A further advantage of the inventive solution is that the use of expensive fiber bundles comprising a randomized arrangement of the individual fibers will not be necessary anymore in the future, and in this way considerable savings can be made in the production of the light conductors on the one hand, and, on the other hand, mechanical problems such as twisting and squashing of the fibers do not occur anymore due to the thermal expansion in use and during autoclaving.

Furthermore, the inventive solution enables a very easy and cost-effective provision of lighting devices or light curing devices whose emitted work spectra can be synthesized by means of additive light mixing of the spectra of light diodes with different emission spectra by electronically controlling the different light diodes respectively. It is especially surprising that due to the specific construction of the inventive solution using only the simplest optical means, a very high degree of homogenization can be achieved with respect to the light intensity and emission spectra across the entire lighting cross section and at the same time the efficiency of the transmission of light can be improved and the power loss can be reduced.

Advantageously, the inventive light mixing device can be positioned ideally with respect to the light diodes or semiconductor light sources. In doing so, the positioning parameters can be selected such that the entry surface of the light mixing member is located "out of focus" with respect to the respective focal points of the light diodes or reflectors assigned to the semiconductor light sources, and is, on the one hand, illuminated possibly over its entire surface by the entry beams or rays and that, on the other hand, the entry angle area of the incoming radiation exploits most completely the entry or acceptance cone predefined by the numerical aperture of the light entry end of the light mixing member.

A further aspect, that often resulted in problems due the large temperature differences during the operation and during the autoclaving process in devices according to the prior art was that the long fibers of the fiber bundle of light conductors as they are usually used in this connection, due to the heat development during the operation and especially during the heat influence during the autoclaving process expand strongly correspondingly, with the longer fibers naturally expanding stronger than the shorter fibers. As typically curved or cranked light conductor fibers are used with such devices, the long fibers of the fiber bundle at the outer side of the curvature expand stronger than the shorter fibers at the inner side of the curvature. Due to this, strong temperature changes resulted in a considerable thermal deformation that could also lead to the misalignment or damage of a glass body that was arranged in the immediate neighborhood thereof. Moreover, displacements and a partial slip is typically the result between the glass fibers and the protective cladding thereof on the one hand, but also with respect to the plastic sleeve surrounding the entire fiber bundle and mechanically stabilizing it, thus causing permanent distortions of the formerly flattened and finely polished light entry and light exit surfaces, whereas in the many years of use due to the frequent strong temperature changes such distortions basically increase in the course of time. The result are increasing displacements of the individual optical fibers with respect to one another, as well as displacements and possible tensions between the fiber bundle and a possible adjacent or abutting optical component, maybe resulting in mechanical and optical problems and adjusting problems. Moreover, a change of the distance of the fibers of the fiber bundle to adjacent optical components may occur and an irregular gap with a undefined, irregular or uneven distance between the fiber bundle and the adjacent optical component may form.

As a further advantage of the inventive solution every unnecessary additional bending in the beam path of the light path is avoided. In particular, any curvatures within a (monocore) light-conducting rod can be omitted which, as it has been shown, result in considerable additional light losses within the light path and worsen the efficiency considerably.

Compared to the flexible monocore light conductor known from the publication DE-OS 23 52 670, the multicore section—as it is used according to the invention—further has the advantage that the yield losses in relation to the straight layout of the light conductor increase far less quickly. A heavily bent multicore light conductor typically has a smaller attenuation than a light conductor curved in the same radius so that according to the invention always a multicore light conductor can be used in the curved or cranked section of the light conductor. In this connection it is particularly favorable if the the multicore section which has a curvature or is cranked, is particularly arranged next to the light exit side end.

Surprisingly, the invention exhibits the further advantage that already a light mixing member with a small overall length that is in the order of the diameter of the light mixing device, is capable of thoroughly mixing the light of LED chips of different color or semiconductor radiation sources or the various emission spectra thereof, so that well-mixed light enters the multicore section of the light conductor and no color variance across the light exit surface of the light conductor can be determined.

The mounting of the light conductor relative to the light source can be effected in any suitable manner, for example with the aid of a bushing that also enables the light conductor to be rotatable relative to the light source and to be removable therefrom. But all other design variations for the use between the light conductor and the lighting or lighting curing device, suggested heretofore in the state of the art, can be combined with the inventive solution without any problems. Thus, the connection interface between the light conductor and the lighting or light curing device can be adapted in any desired way to the technical requirements without the need for developing special solutions thereto.

In a preferred embodiment the light mixing member can be configured in a rotationally symmetric way. Constructively, this represents an especially functional solution that further permits an adaptation, to a large extent, of the optical properties of the light mixing member with respect to the homogenization performance at a given overall length, for instance an adaptation to the geometrically optical radiation paths that are predefined with respect to the light generation device, and further permits any necessary adaptations with respect to the numerical aperture relating to the light entry end of the light mixing member and between the light mixing member and the fiber bundle of the light conductor. Furthermore, it is possible to adapt the size of the light entry surface of the light mixing member to the geometry of the light generation device on the one hand, and, for instance, concentrate the energy of the light onto a fiber bundle with a smaller diameter, on the other hand. Furthermore, for instance curved wall sections or taperings in the cross-section of the light mixing member can influence and modify the angles of reflection of the light beams that are completely internally reflected within the light mixing member, and due to the larger number of wall reflections of the light, the light homogenization within the light mixing member can be further improved.

In a further advantageous embodiment the light mixing member can be configured cylindrically and preferably comprise a planar light entry and/or exit surface. This design of the light mixing member can be realized technically in an especially simple manner and thus it can be produced very cost-effectively, however, with a high degree of homogenization with respect to the intensity distribution and the spectral emission curves across the entire exit surface of the optical fiber bundle being able to be be achieved surprisingly.

In a further preferred embodiment the light entry and exit surface can comprise a polished surface and/or a surface finish or coating or other reflection-reducing coatings and/or is impingeable by an immersion means. With the aid of such a polished surface whose remaining surface roughness preferably amounts to at most a small fraction of the wavelength of light used, the transmission properties of the light mixing member can be improved and light losses can be considerably reduced. Alternatively or additionally, a surface finish or coating or other reflection-reducing coatings can be applied to the light entry and/or exit surfaces of the light mixing member. This measure can further reduce light losses when light passes through the light mixing member. As an alternative or in addition to the above mentioned measures it is also possible to apply an immersion means such as an immersion oil, for instance silicone oil, to the corresponding surfaces of the light mixing member such that the gap between the light mixing member and, for instance, the fiber bundle of the light conductor or the protective glass across light diodes or semiconductor light sources with associated reflectors completely fills up with this immersion means and thus instead of a solid-air-solid phase transition a solid-liquid-solid phase transition takes place. The index of refraction of the immersion means which is higher relative to that of air makes it possible to further reduce light losses due to boundary surface reflection, and then to again carry out adaptations of the numerical aperture of the subsequent optical components.

In a further preferred embodiment the light mixing member can comprise a light-conducting material, preferably with at least one light-conducting core, preferably made of a core glass, comprising a first refraction index and a light-conducting cladding, preferably made of cladding glass, comprising a second refraction index, said second refraction index being smaller—preferably by at least 0.1 units—than the first refraction index. The light-conducting material enables an extremely low-loss conduction of the emitted light power of the light production means and at the same time efficient feed into the light conductor. Such a coaxial design of the light mixing member made of two different transparent materials, preferably of two types of glass, comprising different indices of refraction, radiation losses in connection with total internal reflection can be further reduced and a better guidance of the radiation can be achieved. Contrary to conventional light conductors, just like those widely used in the field of light waveguide technology, in the light mixing member mentioned here there is preferably a clear difference between both indices of refraction of the core and cladding layer, which difference preferably amounts to at least 0.1 units. A relatively larger difference of this kind between the two indices of refraction enlarges the numerical aperture of the light mixing member and also allows for a "catching" of incident light beams which differ substantially from the axis of incidence of the light entry surface of the light mixing member and thus ensures an enlargement of the entry cone for the radiation of the light generation device. As a further advantage, the angular area for the total internal reflection of the radiation conducted in the light mixing member increases and the reflection coefficient is improved considerably. Instead of glasses, other transparent inorganic materials or ceramics but also organic glasses with or without doping or transparent plastic materials can be used for core and/or cladding areas of the light mixing member.

In a further preferred embodiment the light mixing member can comprise a reflection enhancing coating or a reflective sleeve at its circumferential surface. Light losses within the light mixing member can be further reduced with the help of an additional reflective layer of this kind and at the same time the numerical aperture of the light mixing member can be increased considerably such that the angle of acceptance of the light entry cone of the light mixing member can be increased considerably. A further aspect is that the reflection of the light radiation conducted within the light mixing member is taking place at two boundary surfaces in this exemplary embodiment and thus every light beam conducted reflexively within the light mixing member is separated into two respective sub-beams that are offset relative to one another, into one first sub-beam which is partially totally reflected at the boundary layer between core and cladding of the light mixing member, and into a second light beam whose reflection occurs at the reflective outer layer of the light mixing member, thus improving the homogenization performance of the light mixing member even further.

In a further preferred embodiment the diameter of the light mixing member amounts to preferably between 2 mm and 20 mm, particularly preferably between 6 mm and 15 mm, in particular between 8 mm and 13 mm, and the length of the light mixing member is greater than 0.5 times the diameter, in particular greater than 0.8 times the diameter, and preferably smaller than 5 times the diameter, in particular smaller than twice the diameter of the light mixing member. These dimensions represent an especially favorable constructive dimensioning with respect to the geometry of the light mixing member. In this way, an optimal mixing of light and homogenization can be achieved at minimized external dimensions. Additionally, the given diameters take account of the geometrical optical conditions with respect to the size of the light generation device and the entry diameter of the fiber bundle of the light conductor, as it is typically used in the given fields of medicine and dental medicine.

In a further preferred embodiment the light mixing member may be embodied as a hollow body with reflecting side walls. This represents an alternative design with respect to a light mixing member that is made of one or more transparent solid materials. In this connection, it is conceivable to effect the respective radiation guidance in an open air-filled rod-shaped hollow body with reflecting side walls, whereas at the entry and exit side of the light-mixing hollow body for example glass covers may be provided. In the case of such a hermetically sealed light-mixing hollow body the interior thereof may also alternatively filled with an inert or protective gas or in case of a liquid light conductor with a transparent, refractive liquid.

In a further preferred embodiment the light mixing device can comprise a mounting sleeve—preferably made of a highly temperature resistant plastic material, in particular a sulfone, etherketone or imid plastic material or plastic composite material—to which the light mixing member is connected, preferably in a force-fitting and/or in a firmly bonded manner, said mounting sleeve being connectable to at least one of the two, preferably in a self-adjusting manner relative to the light conductor and/or the light generation device. This represents an especially advantageous design for mounting the light mixing member within the beam path of the lighting device or the light curing device. In doing so, the mounting sleeve can be connected to the light conductor and/or to the light generation device at or in the housing of the lighting or light curing device wherein the mounting sleeve is preferably configured such that it adjusts itself with respect to the light conductor and/or the light generation device and is thus positioned exactly within the radiation path without the need for additional mounting and adjusting efforts. In this connection, the mounting sleeve is made at least to a large extent preferably of a highly temperature resistant plastic material, in particular a sulfone, etherketone or imid plastic material or plastic composite material. In this way, the required temperature resistance, mechanical strength and dimensional stability of the mounting sleeve can be maintained on the one hand, and due to the elastic properties of the corresponding plastic materials a capacity to absorb thermal expansion movements and a limitation of thermal stresses is achieved on the other hand. At the same time, a mounting sleeve of this kind made of such a plastic material enabled the targeted use of press fits and/or preloads between the mounting sleeve and the light mixing member on the one hand which in this case can be connected to the mounting sleeve in a preferably force-fitting and/or firmly bonded manner, and on the other hand between the mounting sleeve and the connection component to which the mounting sleeve can be attached free of play and securely in connection with changes of temperature using a press fit and/or preload.

In a further preferred embodiment the light entry and/or light exit surface of the light mixing member can be formed in an aplanar manner. Thus, it is, for instance, possible to configure the respective surfaces of the light mixing member in a slightly wavelike or undulated manner, for instance just like the concentric, circular waves that arise in a water surface after a stone's throw. As a result of such a surface design, incoming and outgoing light beams—in contrast to a planar surface—are deflected slightly in an alternating manner in the radial direction of the light mixing member and are spread across a larger angular area, thus being able to considerably increase the light mixing effect of the light mixing member. A similar effect could be achieved with a faceted surface design or with a Fresnel cut of the respective front sides of the surfaces of the light mixing member. Furthermore, it is also conceivable to configure the respective surfaces of the light mixing member convexly or concavely, in order to thus increase the angles of acceptance for the light entry cone or carry out adaptations with respect to the numerical entry and/or exit aperture and in this way to, for instance, limit the divergence of the exit beam from the light mixing member and adapt it to the numerical aperture of the fiber bundle.

In a further preferred embodiment the light mixing device may be attached within the housing of the lighting device or light curing device, respectively, whereas it preferably may remain there during the replacement of the light conductor. This is a particular simple alternative with respect to both construction and handling. In this manner, the light conductor may be simply individually removed from the housing of the lighting device or light curing device, respectively, and without the light mixing device in order to replace the light conductor with another type of light conductor or to replace the light conductor after use with a freshly sterilized light conductor. In addition, it is conceivable in case of a light mixing device that is fixedly mounted above the light generation device within the housing, and that hermetically seals the light generation device, to protect it from moisture and pollution and/or damage. In this way, it can be done without an additional cover glass covering the light generation device, and efficiency-reducing border surface reflections can be minimized.

In a further preferred embodiment the light mixing device can be provided and configured for retrofitting a lighting device or a light curing device, and is mountable between the light conductor and the housing of the light generation device or the light curing device—preferably in a bushing. This creates the possibility of retrofitting lighting devices or light curing devices, which already exist and are being used, with the advantageous inventive light mixing device and thus improve their efficiency and retrofit them with the inventive advantages at a later stage.

Furthermore, a medical or dental-medical lighting device, in particular a light curing device for the polymerisation of dental masses, having a housing with a light generation device, a light conductor and a light mixing device that is disposed between the light generation device and the light conductor, is provided for the solution to the inventive object, the light mixing device exhibiting the features of the previously mentioned light mixing devices.

In an advantageous design the light mixing device is mountable within the lighting device or the light curing device, respectively, the light conductor being attached to the housing via a mounting sleeve and being separable from the housing and the light mixing device and being autoclavable in particular together with the mounting sleeve after having been separated therefrom. This design is especially favorable with respect to construction, mounting and handling thereof, and enables the above-mentioned advantages. In this connection, the light conductor may simply removed or detached from the housing of the lighting device or light curing device, respectively, and without the light mixing device, in order to replace the light conductor with another type of light conductor or to replace the light conductor after use with a freshly sterilized light conductor. In addition, it is conceivable in case of a light mixing device that is fixedly mounted above the light generation device within the housing, and that hermetically seals the light generation device, to protect it from moisture and pollution and/or damage. In this way, it can be done without an additional cover glass covering the light generation device, and efficiency-reducing border surface reflectance can be minimized.

In a further advantageous design of the medical or dental-medical lighting device, in particular the light curing device for the polymerisation of dental masses, an adjustment and/or press-on device may be disposed between the light mixing device and the light conductor, by means of which—at least indirectly—the light conductor and the light mixing device are connectable to one another in a detachable and preferably elastic manner. Thereby, it is possible, on the one hand, to provide such an adjustment or press-on device with the aid of which the light mixing device is connected with the light conductor in a geometrically optically defined manner, said light mixing device being removed from the device together with the light conductor upon removal thereof, and is only separated from the light conductor in the course of the autoclaving process, preferably prior to the autoclavation. Preferably, however, the light mixing device is arranged in front of the light generation device in the housing and is attached at this position, and the light conductor in turn is connected to the housing via a bushing-sleeve-structure that is embodied as a plug-in connection. In this manner, the above-mentioned adjustment and/or press-on device could be formed via the plug-in structure, by means of which the light conductor is indirectly detachably positioned and adjusted relative to the light mixing device, whereas the respective connection in the fixed or locked condition preferably is also formed to be elastic. Hereby, a simple and reliable adjustment and positioning of the mentioned optical components can be ensured, with a pretension being able to be built up due to the elasticity that reliably ensures a gap-free positioning of the optical components across the entire operating temperature range.

In a further preferred embodiment of the medical or dental-medical lighting device, in particular a light curing device for the polymerisation of dental masses, the adjustment and/or press-on device enables the light conductor to be impinged with a press-on pressure in the direction of the light mixing device, enabling the defined positioning of the light exit surface of the light mixing member with respect to the light entry surface of the light conductor. In this embodiment, the adjustment and/or press-on device ensures a defined press-on pressure and thus a defined pretensioning between the light conductor and the light mixing device, which components in this manner can be positioned in a reliable and gap-free relationship with one another across the entire operating temperature range. Hereby, for instance, it is also conceivable to provide a stop between respective leveled surfaces of highest quality of light mixing devices and light conductors, or to apply or vapor deposit a thin spacer in the outer peripheral area of one of the two optical surfaces in order to adjust or give a defined constant gap between the exit surface of the light mixing device and the entry surface of the light conductor. In the case of a micro spacer that for example may be formed with the aid of vapor deposition on one of the two optical surfaces, hereby also a submicroscopic gap of less than a quarter of the wavelength may be produced, with the aid of which boundary surface reflections at the optical surfaces of light mixing member and light conductor could be eliminated to the greatest possible extent. Generally, however, it will be sufficient to set a gap in the order of approximately 100 to 200 µm.

In a further preferred embodiment of the medical or dental-medical lighting device, in particular a light curing device for the polymerisaiton of dental masses, the adjustment and/or press-on device can have an elastic expansion reserve between the light mixing device and the light conductor, in particular for maintaining the press-on pressure and/or for ensuring the adjustment while at the same time providing an offset or alignment capability for thermal expansion movements. Due to such an elastic expansion reserve, a particularly reliable positioning and adjustment between the light conductor and the light mixing device can be ensured and maintained for all temperatures and all operating conditions, whereby due to the elasticity a pretensioning can be built up that reliably ensures a gap-free positioning of the optical components across the entire operating temperature range.

In a further preferred embodiment of the medical or dental-medical lighting device, in particular the light curing device for the polymerization of dental masses, the adjustment and/or press-on device may comprise at least one spring element, in particular an annular spring element that locks in place with the recesses of sleeve or bushing, in particular with annular grooves of the sleeve and bushing, said spring element interacting with the shape and/or the arrangement of the recesses, in particular the annular grooves, such that a press-on pressure of the light conductor in the axial direction of the light mixing member may be generated against the same. This is a particularly simple, reliable and proven constructional embodiment of such an adjustment and/or press-on device. Preferably, such an annular spring element may for example be be employed as an O-ring made of a highly elastic silicone material, whereby respective annular grooves of the sleeve and bushing are slightly axially displaced to one another so that the silicone O-ring is not only pretensioned in the radial direction but also in the axial direction when it is inserted and locks in place so that it ensures the above-described axial press-on pressure of the two optical components against one another or against a corresponding stop, respectively, and in this manner provides for a precise spacing of the respective surfaces. However, it would also be conceivable to provide such spring elements in many other ways and, for example, to provide spring-loaded, radially guided balls in the bushing area of the housing, which balls may lock in place with a corresponding annular groove within the sleeve of the light conductor. It is advantageous, however, if the adjustment and/or press-on device is embodied so that the bushing of the light conductor is both twistable in relation to the housing of the lighting device and/or the light curing device and is detachably mountable thereon.

Apart from that it can also be advantageous to provide light conductors that are multicore along the entire length thereof or in a section thereof, and at the same time have conical individual fibers in at least sections thereof or in which a conically running monocore light-conducting section is used so that such a light conductor especially tapers towards the light exit side end and thus focuses the entire radiated power of the light generation device on a small area at the exit side, thus increasing the power and energy density of the illuminated or light- or radiation-impinged area.

The present invention hereinafter is explained in more detail in connection with the embodiments illustrated in the attached drawings.

Further advantages, details and features emerge from the following description of the exemplary embodiment of the invention in conjunction with the drawings in which FIG. 1 shows a schematic sectional view of an embodiment of an inventive light mixing device mounted between a light generation device of a light curing device for the polymerisation of dental masses and a light conductor for irradiating the dental mass to be cured.

Figure 2:
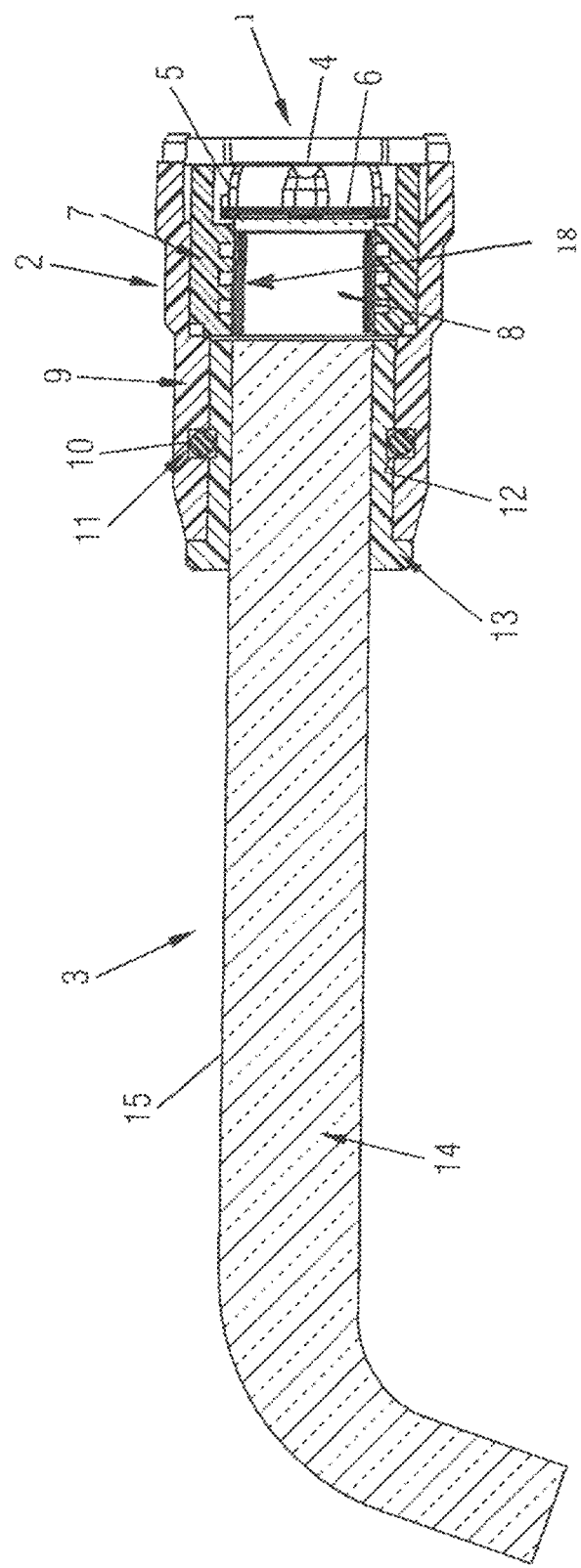

FIG. 2 shows a schematic sectional view of an embodiment of an inventive light mixing device having a reflective coating.

FIG. 1 shows a light generation device 1 of a light curing device for the polymerisation of dental masses having a light mixing device 2 subsequently attached thereto in the radiation path, said light mixing device 2 being arranged between the light generation device 1 and the light conductor 3. The light generation device 1 comprises a carrier with light emitting diodes 4 arranged thereon that differ from each other with respect to their emission spectra. The light of the light diodes is hereby bundled or focused in the direction of the light mixing device and light conductor with the aid of reflectors 5. A mineral protective glass 6 is arranged in front of these light diodes 4 and reflectors 5 that has an anti-reflective coating on both sides in order to minimize light losses and reflections at the phase transition of the light between air and solid or solid and air, respectively, on both the entry and exit side.

The light mixing device 2 comprises a holder 7 made of a temperature resistant plastic such as a fiber-reinforced polysulfone plastic material, and the light mixing member 8. With the aid of the holder 7, the light mixing member 8 is hereby arranged and held in the light path at a defined distance of 100 µm to 200 µm behind the protective glass 6 in the housing. The light mixing member has a diameter of 10 mm and a length of 8 mm and thus completely covers the entire area of the light generation device 1 including the reflectors 5 up to its inner outer contour on the light entry side. The light mixing member 8 hereby consists of an inner core (not shown in the drawing), which core is made of a highly refractive core glass with an index of refraction of 1.6 that is coaxially surrounded by a sheath glass layer with an index of refraction of 1.5 that additionally comprises a reflection protective coating 18 at its outer peripheral side and—subsequently outwardly thereto—a thin plastic protective coating.

The entire light mixing member 8 is hereby shaped to have cylindrical shape, with flat ground and fine polished light entry and exit surfaces whose remaining surface roughness is in a range of less than 100 nm, and which further have an anti-reflective coating. The light mixing member 8 is attached within the holder 7 in a force-fitting manner and is additionally secured with a special adhesive and is hermetically sealed against the holder. The holder 7 radially surrounds a plastic bushing 9 that is attached to the housing (not illustrated) and that represents parts of the plug-in holder for the light conductor 3. The cylindrical plastic bushing 9 comprises at its inner peripheral side an annular groove 10 into which an O-ring 11 made of silicone is inserted. Said O-ring 11 is in snap-in connection with a corresponding annular groove 12 in a plastic sleeve part 13 made of a fiber-reinforced polysulfonate plastic material and thus keeps the sleeve part in position and under pretension relative to the light mixing device 2. Within the plastic sleeve 13 that is embodied as to be hollow, the light conductor 3 is arranged that comprises a double butted fiber bundle and a firmly bonded, protective and reinforcing plastic cover 15 surrounding the entire fiber bundle, the cover in turn being firmly bonded to the plastic sleeve 13 via adhesive bonding.

In this exemplary embodiment the adjustment between the light entry surface of the light conductor 14 and the light exit surface of the light mixing member 8 is effected indirectly via the plastic sleeve 13 having a collar at its distal end that due to the O-ring 11 is preloaded against the plastic bushing 9, whereby the light mixing member 8 within the plastic bushing 9 via its holder 7 is hold in its exact position, however, is configured and attached as to rotate about the axial axis. In this manner, a constant spacing of approximately 100 µm is also ensured between the light exit side surface of the light mixing member 8 and the light entry side surface of the light conductor 14. The light conductor 3 hereby is accommodated within the plastic holder 9 with its O-ring 10 made of highly elastic silicone via its plastic sleeve 13 as to rotate therein. The light entry side diameter of the fiber bundle 14 exactly corresponds to the light exit side diameter of the light mixing member 8 and amounts to 10 mm, whereas the distal end of the fiber bundle 14 uniformly tapers towards the light exit position to 8 mm. The light emitting diodes 4 may be electronically controlled separately, in order to set and monitor their power individually, on the one hand in order to be able to operate the light emitting diodes till the maximal limit performance, without overloading or damaging them, and on the other hand in order to be able to control their light power independently. Through this, light diodes with different emission spectra can be controlled such that by means of additive color mixing a desired light color and/or a desired emission spectrum can be provided by the plurality of light emitting diodes and can be mixed and homogenized within the light mixing member 8. The light conductor 3 close to its distal end comprises a curvature with an offset angle of about 60 degrees with respect to the light entry axis.

All details and values of the embodiment described are only to be understood as being exemplary and can be modified within the scope of protection of the claims. Even if the invention is described here in conjunction with the use in a dental light curing device, it is to be understood that the basic ideas of the invention are also employed advantageously in other apparatuses requiring a light conductor, in particular in medical devices such as endoscopes or other light sources, for instance, for medical research, the use in a laboratory or industrial purposes.

The invention claimed is:

1. A medical or dental-medical lighting device comprising
a housing with a light generation device,
a light conductor,
a light mixing device positioned between the light generation device and the light conductor and comprising
a bar-shaped light mixing member formed cylindrically and having a planar or flat light entry and light exit surface and a holder through which the light mixing device is mountable and is held in position separably from the light conductor, wherein the holder of the light mixing device is radially surrounded by a bearing bushing comprising a first recess on an inner side of a circumference, wherein via said first recess, a spring element and a second recess in a hollow bearing sleeve, within which hollow bearing sleeve the proximal end of the light conductor is located, a snap-in connection of light mixing device and light conductor can be produced.

2. The medical or dental-medical lighting device according to claim 1, wherein the bearing sleeve comprises a collar at its distal end.

3. The medical or dental-medical lighting device according to claim 1, wherein the light conductor comprises a fiber bundle having a distal end that tapers and a firmly bonded, protective and reinforcing plastic cover surrounding the entire fiber bundle, the cover in turn being connected to the bearing sleeve via adhesive bonding.

4. The medical or dental-medical lighting device according to claim 1, wherein the light conductor, close to its distal end, comprises a curvature with an offset angle of about 60 degrees with respect to a light entry axis.

5. The medical or dental-medical lighting device according to claim 1, wherein the bearing sleeve and the bearing bushing comprise plastics.

6. The medical or dental-medical lighting device according to claim 1, wherein the light mixing member is formed in a rotationally symmetric manner.

7. The medical or dental-medical lighting device according to claim 1, wherein the light entry and/or light exit surface comprises a polished surface and/or a surface finish or reflection-reducing coating and/or is subjectable to an immersion means.

8. The medical or dental-medical lighting device according to claim 1, wherein the light mixing member comprises a light conducting material, with at least a light-conducting core and with a light-conducting sheath.

9. The medical or dental-medical lighting device according to claim 8, wherein the light-conducting core is made of a core glass having a first refractive index, and wherein the light-conducting sheath is made of a cladding glass having a second refractive index, the second refractive index being lower than the first refractive index.

10. The medical or dental-medical lighting device according to claim 9, wherein the second refractive index is at least 0.1 units lower than the first refractive index.

11. The medical or dental-medical lighting device according to claim 1, wherein the light mixing member comprises a reflection-enhancing coating or a reflective sleeve on a circumferential surface.

12. The medical or dental-medical lighting device according to claim 1, wherein the diameter of the light mixing member is between 2 mm and 20 mm and the length of the light mixing member is greater than 0.5 times the diameter, and smaller than 5 times the diameter of the light mixing member.

13. The medical or dental-medical lighting device according to claim 12, wherein the diameter of the light mixing member is between 6 mm and 15 mm, and the length of the light mixing member is greater than 0.8 times the diameter, and smaller than 2 times the diameter of the light mixing member.

14. The medical or dental-medical lighting device according to claim 12, wherein the diameter of the light mixing member is between 8 mm and 13 mm.

15. The medical or dental-medical lighting device according to claim 1, wherein the light mixing device comprises a mounting sleeve, with which sleeve the light mixing member is connected non-positively and/or in a firmly bonded way, the mounting sleeve, with respect to the light conductor and/or the light generation device, being connectable in a self-adjusting manner to at least one of the two components.

16. The medical or dental-medical lighting device according to claim 15, wherein the mounting sleeve is made of a high-temperature resistant plastic.

17. The medical or dental-medical lighting device according to claim 16, wherein the high-temperature resistant plastic comprises a sulfone, ether ketone, imide plastic, or plastic composite material.

18. The medical or dental-medical lighting device according to claim 1, wherein the mixing member comprises at least one light entrance and/or exit surface, the at least one light entrance and/or exit surface of the light mixing member formed in a planar fashion.

19. The medical or dental-medical lighting device according to claim 1, wherein the light mixing device is mountable in the housing of the lighting device, and can remain in the housing when exchanging the light conductor.

20. The medical or dental-medical lighting device according to claim 1, wherein the light mixing device is provided and configured for retrofitting a lighting device or a light curing device and is mountable between the light conductor and the housing of the light generation device or the light curing device.

21. The medical or dental-medical lighting device according to claim 20, wherein the light mixing device is mountable in the bearing bushing.

22. The medical or dental-medical lighting device according to claim 1, wherein the device is a light curing device for the polymerisation of dental masses and wherein the bar-shaped light mixing member is made with at least one transparent material.

23. The medical or dental-medical lighting device according to claim 22, wherein the at least one transparent material comprises glass.

24. The medical or dental-medical lighting device according to claim 1, wherein the first recess is a first annular groove and the second recess is a second annular groove.

25. A light curing device for the polymerisation of dental masses, comprising
a housing with a light generation device,
a light conductor and
a light mixing device,
the light mixing device being disposed between the light generation device and the light conductor, wherein a holder of the light mixing device is radially surrounded by a bearing bushing comprising a first recess on the inner side of the circumference, via which first recess, a spring element and a second recess of a hollow bearing sleeve, within which the proximal end of the light conductor is located, a snap-in connection of the light mixing device and the light conductor can be produced, and
wherein the light mixing device is formed cylindrically having a planar or flat entry light entry and exit surface.

26. The light curing device for the polymerisation of dental masses, according to claim 25, wherein the bearing sleeve comprises a collar at its distal end.

27. The light curing device for the polymerisation of dental masses, according to claim 25, wherein the light mixing device is mountable in the housing of the light curing device, the light conductor being attachable to the housing via the bearing sleeve and being separable from the housing and the light mixing device and after separation being autoclavable together with the bearing sleeve.

28. The light curing device for the polymerisation of dental masses, according to claim 25, wherein between the light mixing device and the light conductor an adjustment and/or press-on device is disposed via which, at least indirectly, the light conductor and the light mixing device are connectable in a detachable and elastic way.

29. The light curing device for the polymerisation of dental masses, according to claim 25, wherein by the adjustment and/or press-on device the light conductor is subjectable to a press-on pressure towards the light mixing device whereby the light exit surface of the light mixing member can be positioned in a defined way with respect to the light entry surface of the light conductor.

30. The light curing device for the polymerisation of dental masses, according to claim 25, wherein the adjustment and/or press-on device between the light mixing device and the light conductor comprises an elastic expansion reserve, for maintaining the press-on pressure and/or for ensuring the adjustment and having an alignment ability for thermal expansion movements.

31. The light curing device for the polymerisation of dental masses, according to claim 25, wherein the adjustment and/or press-on device comprises at least the spring element, which locks in place with the recesses of the bearing sleeve and/or the bearing bushing, the spring element interacting with the shape and/or disposition of the recesses, such that a press-on pressure of the light conductor in the axial direction of the light mixing member can be produced against the same.

32. The light curing device for the polymerisation of dental masses, according to claim 31, wherein the spring element comprises an annular spring element and the recesses of the bearing sleeve and the bearing bushing are annular grooves.

33. A medical or dental-medical lighting device comprising
a housing with a light generation device,
a light conductor,
a light mixing device positioned between the light generation device and the light conductor and comprising
a light mixing member formed as a hollow body with reflective side walls and having a light entry and light exit surface and
a holder through which the light mixing device is mountable and is held in position separably from the light conductor,
wherein the holder of the light mixing device is radially surrounded by a bearing bushing comprising a first recess on an inner side of a circumference,
wherein via said first recess, a spring element and a second recess in a hollow bearing sleeve, within which hollow bearing sleeve the proximal end of the light conductor is located, a snap-in connection of light mixing device and light conductor can be produced.

* * * * *